United States Patent
Smillie et al.

(10) Patent No.: US 9,820,717 B2
(45) Date of Patent: Nov. 21, 2017

(54) APPARATUS AND METHOD FOR FETAL IMAGE RENDERING

(71) Applicant: Toshiba Medical Systems Corporation, Otawara-shi (JP)

(72) Inventors: Antonia L Smillie, Edinburgh (GB); Magnus Wahrenberg, Edinburgh (GB); Timothy Day, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/774,314

(22) Filed: Feb. 22, 2013

(65) Prior Publication Data

US 2014/0243670 A1    Aug. 28, 2014

(51) Int. Cl.
*A61B 8/00* (2006.01)
*A61B 8/08* (2006.01)

(52) U.S. Cl.
CPC ............ *A61B 8/0866* (2013.01); *A61B 8/463* (2013.01); *A61B 8/465* (2013.01); *A61B 8/466* (2013.01); *A61B 8/483* (2013.01); *A61B 8/5207* (2013.01)

(58) Field of Classification Search
CPC ....... G01S 7/52071; A61B 8/12; A61B 8/463; A61B 8/465; A61B 8/466; A61B 8/483; A61B 8/0866; A61B 8/5207; G06T 15/08; G06T 2210/41
USPC .......................... 600/437–469; 382/128–132
See application file for complete search history.

(56) References Cited

U.S. PATENT DOCUMENTS

| | | | | |
|---|---|---|---|---|
| 6,063,030 A | * | 5/2000 | Vara | A61B 8/468 600/437 |
| 6,254,540 B1 | * | 7/2001 | Kikuchi | A61B 8/00 128/916 |
| 6,468,212 B1 | * | 10/2002 | Scott | A61B 8/00 600/437 |
| 8,519,998 B2 | * | 8/2013 | Hashimoto | A61B 8/06 345/424 |
| 2005/0203417 A1 | * | 9/2005 | Okuno | A61B 8/0841 600/463 |
| 2006/0184028 A1 | * | 8/2006 | Wen | G01S 7/52071 600/441 |
| 2006/0241428 A1 | * | 10/2006 | Kao | A61B 8/14 600/437 |
| 2007/0014446 A1 | * | 1/2007 | Sumanaweera | G06T 15/08 382/128 |
| 2009/0124907 A1 | * | 5/2009 | Bruce | A61B 8/481 600/458 |
| 2010/0022880 A1 | * | 1/2010 | Sathyanarayana | A61B 5/02007 600/443 |

(Continued)

FOREIGN PATENT DOCUMENTS

| | | |
|---|---|---|
| JP | 60-202318 | 10/1985 |
| JP | 9-308632 | 12/1997 |
| JP | 2005-323258 | 11/2005 |

*Primary Examiner* — Sanjay Cattungal
(74) *Attorney, Agent, or Firm* — Oblon, McClelland, Maier & Neustadt, L.L.P.

(57) ABSTRACT

Certain embodiments provide an image data processing apparatus, comprising a data receiving unit configured to receive image data that is representative of a fetus, a color determination unit for determining a color based on a property of a parent of the fetus, and a rendering unit configured to render using the determined color an image of at least part of the fetus from the image data.

10 Claims, 5 Drawing Sheets

(56) References Cited

U.S. PATENT DOCUMENTS

| | | | |
|---|---|---|---|
| 2010/0056924 A1* | 3/2010 | Powers | A61B 8/481 600/458 |
| 2011/0162673 A1* | 7/2011 | Samain | A45D 44/005 132/317 |
| 2012/0128218 A1* | 5/2012 | Amyot | G06T 19/00 382/128 |
| 2012/0245465 A1* | 9/2012 | Hansegard | A61B 8/466 600/443 |
| 2013/0182926 A1* | 7/2013 | Lee | G06K 9/00671 382/131 |
| 2014/0073925 A1* | 3/2014 | Kho | A61B 8/483 600/443 |

* cited by examiner

APPARATUS AND METHOD FOR FETAL IMAGE RENDERING

FIELD OF THE INVENTION

Embodiments described herein relate generally to a method of, and apparatus for, fetal image data processing, for example processing of fetal ultrasound image data.

BACKGROUND

It is known to use ultrasound to image a fetus in the womb by transmission and reception of ultrasound waves from a transducer.

Three-dimensional (3D) ultrasound images may be obtained by using software to combine ultrasound data that has been taken at different positions or angles, and to render an image from the combined data using methods such as simple surface shading or direct volume rendering. In four-dimensional (4D) ultrasound imaging systems, a series of three-dimensional images obtained at different times is dynamically rendered to produce a moving 3D image, for example a 3D ultrasound movie.

In recent years, 3D and 4D ultrasound images have been made more realistic through the use of advanced lighting techniques (referred to as global illumination, gradient free lighting, subsurface scattering or photon mapping) that simulate illumination with a more physically accurate model than was previously used.

Although ultrasound images may in principle be rendered using any color, 3D and 4D fetal ultrasound images are usually rendered in a standard color, a sepia or golden-yellow color.

Many parents are having 3D and 4D ultrasound scans in order to bond better with their unborn child, motivated by the realistic appearance of the scans. 3D or 4D ultrasound scans can also be useful for informing parents of the appearance of a fetus that has an abnormality such as a cleft lip or cleft palate. However, the standard color used to render the images is not realistic.

BRIEF DESCRIPTION OF THE DRAWINGS

Embodiments are now described, by way of non-limiting example, and are illustrated in the following figures, in which.

DETAILED DESCRIPTION

Certain embodiments provide an image data processing apparatus comprising a data receiving unit configured to receive image data that is representative of a fetus, a color determination unit for determining a color based on a property of a parent of the fetus, and a rendering unit configured to render using the determined color an image of at least part of the fetus from the image data.

Certain embodiments also provide a method of producing a fetal image, comprising receiving image data that is representative of a fetus, determining a color based on a property of a parent of the fetus, and rendering using the determined color an image of at least part of the fetus from the image data.

Figure 1:
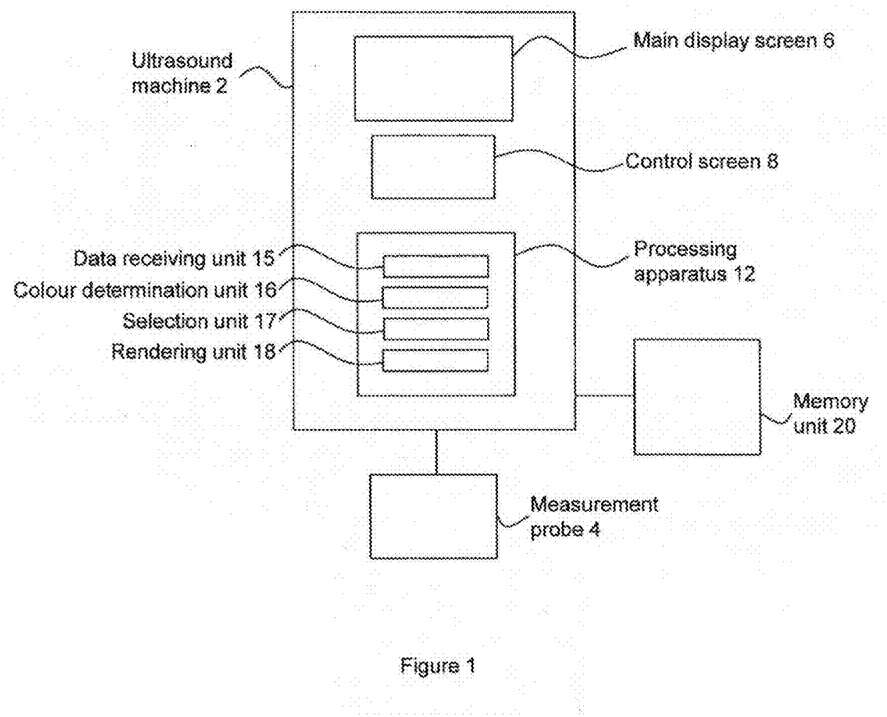
FIG. 1 is a schematic diagram of an image data processing system according to an embodiment.

An image data processing apparatus according to a first embodiment, which is configured to produce a fetal ultrasound image, is illustrated schematically in FIG. 1. The apparatus comprises an ultrasound machine 2 and an associated measurement probe 4. The ultrasound machine has a hardware specification similar to the Toshiba Aplio 500 and the measurement probe 4 is a volume imaging transducer such as the Toshiba PVT-375SBT. Any suitable type of ultrasound machine 2 and measurement probe 4 may be used, for example any ultrasound machine 2 and transducer probe 4 that are configured to obtain fetal ultrasound image data that is suitable for 3D imaging.

The ultrasound machine 2 comprises a main display screen 6 for displaying a main ultrasound image, and a control screen 8. In this embodiment, the control screen 8 is a touch screen, which is both a display device and a user input device. The machine 2 also includes other user input devices, such as input buttons or knobs, a computer keyboard, mouse or trackball. In an alternative embodiment (not shown), a single screen serves as both main display screen 6 and control screen 8. In a further embodiment (not shown), the control screen 8 is a display screen only, and the apparatus also comprises a user input device or devices, such as input buttons or knobs on the ultrasound machine, or a computer keyboard, mouse or trackball. Further embodiments comprise a control screen 8, display screen or main display screen 6 that do not form part of the ultrasound machine 2.

The ultrasound machine 2 comprises a processing apparatus 12 for processing of data, including image data. The processing apparatus 12 includes a data receiving unit 15 for receiving image data that is representative of a fetus, a color determination unit 16 for determining a color based on a property of a parent of the fetus; and a rendering unit 18 for rendering an image of at least part of the fetus from the image data, and for rendering the image in the determined color. The processing apparatus 12 shown in FIG. 1 also includes a selection unit 17. In this embodiment, the data receiving unit 15, color determination unit 16, rendering unit 18 and color selection unit 17 are each implemented in the processing unit 12 by means of a computer program having computer-readable instructions that are executable to perform the method of the embodiment. However, in other embodiments each unit may also be implemented in software, hardware or any suitable combination of hardware and software. In some embodiments, the various units may be implemented as one or more ASICs (application specific integrated circuit) or FPGAs (field programmable gate array).

The processing apparatus 12 also includes a hard drive and other components including RAM, ROM, a data bus, an operating system including various device drivers, and hardware devices including a graphics card. Such components are not shown in FIG. 1 for clarity. In an alternative embodiment, the processing apparatus is not part of the ultrasound machine and is, for example, a personal computer.

Figure 2:
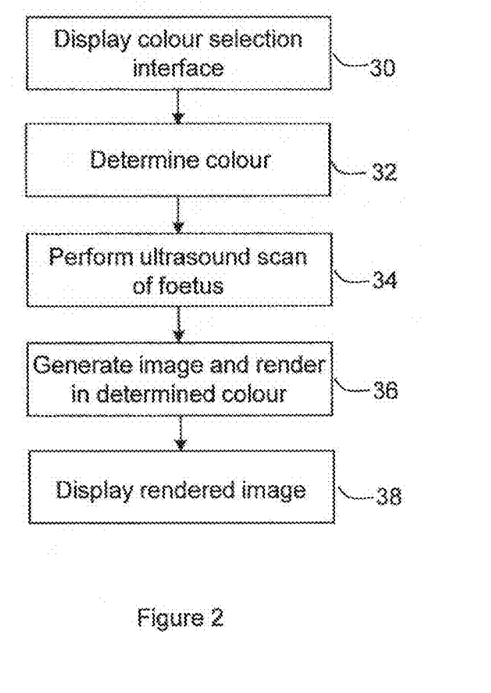
FIG. 2 is a flowchart illustrating in overview a mode of operation of the embodiment of FIG. 1.

The system of FIG. 1 is configured to perform a process having a series of stages as illustrated in overview in the flow chart of FIG. 2

At the first stage 30, the selection unit 17 causes the control screen 8 to present a selection interface showing a plurality of predetermined settings. In this embodiment, the predetermined settings are predetermined colors, which are displayed as an array of icons 40 as shown schematically in FIG. 3. Each icon 40 has a color that represents a different human skin color, also referred to as skin tone. The range of colors displayed may represent the range of all human skin colors. Alternatively, the range of colors may represent the range of skin colors that are most prevalent in the geographical region (for example, the continent or country) in which the ultrasound machine is located, or any other appropriate range of skin colors.

Figure 3:
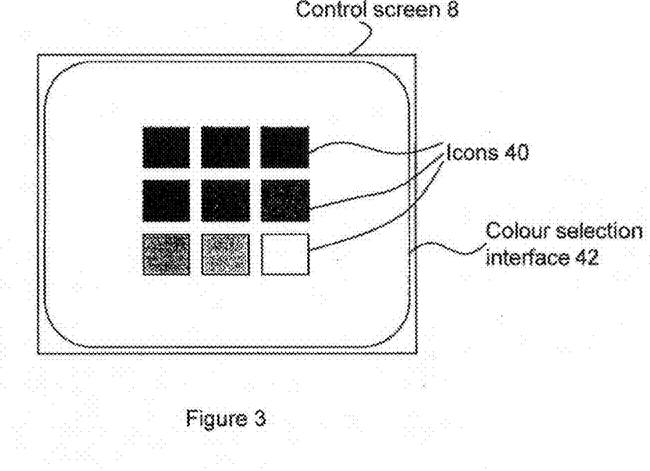
FIG. 3 is a schematic illustration of a color selection interface, comprising an array of icons corresponding to predetermined color settings, in accordance with the first embodiment.
Figure 4:
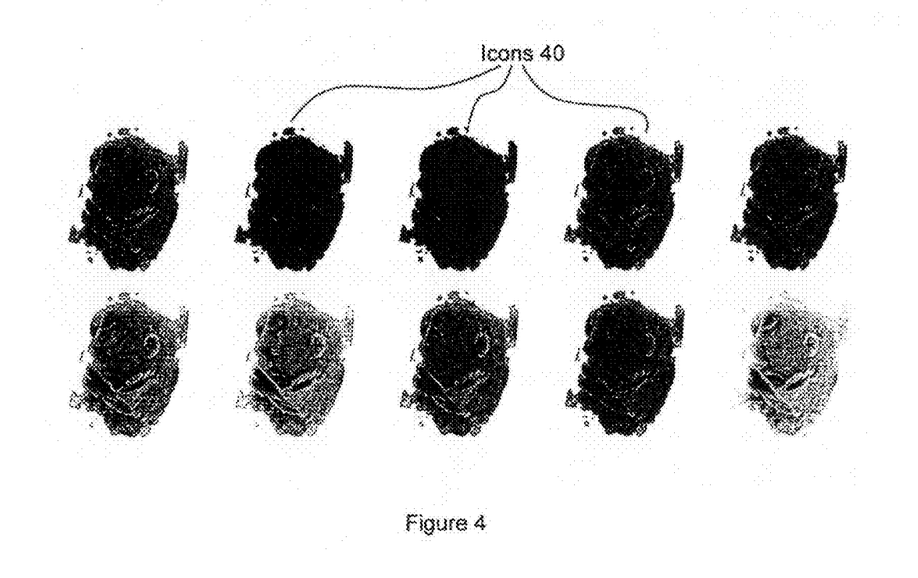
FIG. 4 illustrates further examples of icons for the color selection interface of the first embodiment.

FIG. 3 is a schematic illustration of a selection interface in which the icons 40 are filled squares. The icons may have any other appropriate graphical form, for example the generic fetal images illustrated in FIG. 4. Instead of the grid arrangement illustrated in FIGS. 3 and 4, the arrangement of icons on the control screen 8 may be any other appropriate arrangement, for example, a line, a color wheel, or a continuous color selection bar or area composed of a plurality of contiguous icons.

At stage 32, the operator (for example, a sonographer) selects an icon by touching the control screen 8, which is used as a user input device. Alternatively, the operator may use another input method such as pressing a button or clicking with a mouse. The operator selects the icon that displays the color that is closest to the skin color of the pregnant woman. The color determined by the color determination unit 16 is the color of the selected icon 40.

At stage 34, the operator uses a transducer probe 4 to scan the abdomen of a pregnant woman to obtain image data that is representative of the fetus that she is carrying. The data receiving unit receives this data from the transducer probe. In an alternative embodiment, the data receiving unit retrieves previously-taken image data from the memory unit 20. The memory unit 20 may be part of the ultrasound machine, or part of a separate PC. Alternatively, the memory unit 20 may be a data recording device such as a DVD, USB stick, SD card or mobile phone memory. In alternative embodiments, the data receiving unit retrieves image data from a Picture Archiving and Communications System (PACS) or other remote source. The memory unit 20 may be accessed remotely, for example over a network, wirelessly or over the Internet.

At stage 36, the rendering unit 18 renders a 3D image of at least part of the fetus from the image data that was obtained or retrieved at stage 30, using a 3D rendering technique such as direct volume rendering or a more advanced volume rendering technique such as photon mapping. The rendering unit 18 renders an image that is lit and shaded using an optical simulation model. The determined color is used as a parameter for the optical simulation model. The rendered image can be considered to be in the determined color, subject to the lighting and shading effects of the optical simulation model.

At the final stage 38, the three-dimensional rendered image is displayed on the main display screen 6 of the ultrasound machine 2. The rendered image, having a color that resembles the skin color of the mother of the fetus, presents a more realistic impression than an image that is rendered in the standard sepia color.

In a variant of the first embodiment, two color selection interfaces 42 are displayed in turn at stage 34. The operator selects a first color from the first color selection interface. The second color selection interface then displays a range of colors that are variants of the first selected color, and may include the first selected color. The operator selects a second color from the second color selection interface. The color determination unit 16 determines the determined color to be this second selected color. This method may provide a finer gradation of colors in the second color interface than in the first color interface.

In a further embodiment, the property of a parent on which the determined color is based is the ethnicity of the mother of the fetus, who is pregnant with the fetus. Ethnicity as used here is a term that describes an ethnic group or race (for example, Caucasian, African American)

The selection unit 17 causes the control screen 8 to display an ethnicity selection interface showing a plurality of predetermined settings, in which the predetermined settings are ethnicities. The predetermined settings may be displayed as icons 40, as a text list, including a drop-down list, or by any other suitable method. Each icon 40 or list entry represents a different ethnicity. The operator selects the ethnicity closest to the ethnicity of the pregnant woman by touching the touch screen or by any other suitable input method, for example by operation of a knob, slider or wheel. The color determination unit 16 determines a color that is representative of the selected ethnicity.

Given that within a particular ethnicity there will be a range of skin colors, in certain embodiments an ethnicity selection interface is first displayed under control of the selection unit 17, to enable the operator to select an ethnicity, then a color selection interface in which the range of colors of the icons 40 is representative of a range of skin colors associated with the selected ethnicity. The color determination unit 16 determines a color that is the color selected by the operator from the color selection interface 42.

In another embodiment, the selection unit 17 causes the control screen 8 to display a geographical selection interface showing a plurality of predetermined settings, in which the predetermined settings comprise different geographical regions (for example Western Europe, Southern Africa) or countries (for example Norway, Japan). The regions or countries may be displayed as a text list, including a drop-down list; displayed graphically, for example in a map or as country outlines; or displayed by any other suitable method. The operator selects a region or country, for example the region or country where the measurement is being performed, or the region or country in which the pregnant woman was born. Optionally, the control screen 8 then displays a color selection interface 42 with icons 40 of a range of colors that is representative of a range of skin colors associated with the selected region or country. The color determination unit 16 accordingly determines a color that represents a skin color that is typical of the region or country, or is the color that is selected from the color selection interface 42.

In a further embodiment, geographical information is stored as a default setting of the ultrasound machine. For example, a geographical selection interface is displayed as part of installation or configuration of the ultrasound machine, and the installer selects the geographical location of the machine which is then used as a default setting to determine the range of skin colors displayed on a color selection interface.

Several combinations of selection interfaces have been described above, for example two successive color selection interfaces or an ethnicity selection interface followed by a color selection interface. It is possible to combine any number of such interfaces, of any type, in any order: for example, a geographical selection interface followed by an ethnicity selection interface, followed by one or more color selection interfaces. Any other suitable property of a parent may be used in a selection interface. Although the embodiments above describe selection based on skin color of the mother of the fetus, who is pregnant with the fetus, selection may instead be based on the skin color of the father of the fetus. In the case where the pregnant woman is not a genetic parent of the fetus (for example, where a donor egg has been used), selection may be based on the skin color of a genetic parent of the fetus. Information about skin color may be observed by the operator, provided by a parent, read from a patient record or obtained by any other suitable method. A patient record may be a record held on a Hospital Information System or Radiology Information system, a previous scan, or hospital records. Similar considerations apply to ethnicity or geographical selection.

The embodiment of FIG. 1 can provide for display of fetal images in a more realistic color, which can more accurately anticipate the predicted birth color of the baby.

The next embodiment is directed towards sensing, rather than selection, of a parent's skin color. This embodiment uses the apparatus of FIG. 1 with the measurement probe 4 of FIG. 5. A color sensor 50 and light 52 are located on a measurement probe 4 as illustrated schematically in FIG. 5. The color sensor 50 is provided to sense a skin color or colors of a parent, and the light 52 is provided to illuminate the parent's skin to enable use of the color sensor.

In the discussion below, the color sensor is described as sensing a skin color. However, in practice the color sensor may sense multiple skin colors at the same time, for example where the color sensor comprises multiple pixels, and the skin color of the parent varies across the field of view of the sensor, or lighting conditions vary. In this case the skin colors sensed by the color sensor may be combined by the color determination unit 16 to determine a single representative skin color using any suitable method, for example by averaging. All references to sensing of a skin color below also include sensing and processing of multiple skin colors to determine a skin color.

Figure 5:
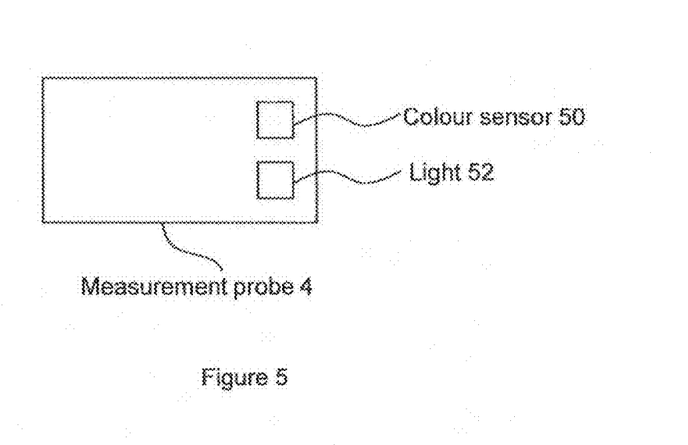
FIG. 5 is a schematic diagram of a transducer probe according to an embodiment.

In the embodiment of FIG. 5, the measurement probe 4 is a volume imaging transducer probe that is configured to obtain image data that is representative of the interior of a subject, for example a patient, and the color sensor 50 can be used to determine a skin color of the subject. When used on a pregnant woman, the measurement probe 4 is able to acquire image data representative of the fetus present within the pregnant woman. Any other suitable measurement probe may be used. Locating the color sensor 50 and light 52 on the transducer probe enables operation of the color sensor 50 and light 52 while the ultrasound scan is being performed, or as part of the same overall procedure. In alternative embodiments, the color sensor 50 and light 52 are located on a separate unit or units. In this particular embodiment, the color sensor is a CCD and the light is a white LED.

Figure 6:
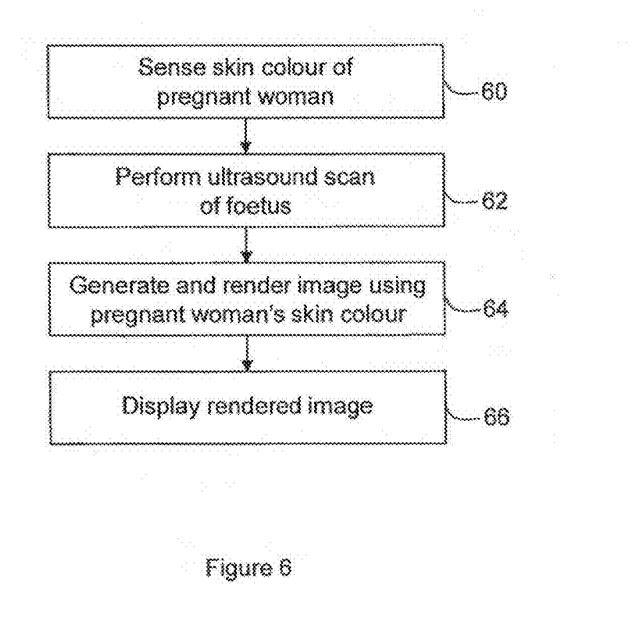
FIG. 6 is a flowchart illustrating in overview a mode of operation of an embodiment using the transducer probe of FIG. 5 with the system of FIG. 1.

The system of FIG. 1 with the measurement probe 4 of FIG. 5 is configured to perform a process as illustrated in the flow chart of FIG. 6.

At the first stage 60, the skin color of the pregnant woman is sensed using the color sensor 50, with the skin illuminated by the light 52. In this embodiment, the sensing is performed automatically as the transducer probe 4 is moved near to the pregnant woman's abdomen to start the ultrasound scan. When the transducer probe 4 is near to the skin but not yet touching, the light 52 illuminates the abdomen and the color sensor 50 senses the skin color of the abdomen and passes color data to the color determination unit 16. In alternative embodiments, the sensing is initiated by the operator, for example by pressing a button on the transducer probe, or through commands on a skin color sensing interface displayed by the control screen 8. In some embodiments, a color sensor is used to sense the skin color on a different part of the body rather than on the abdomen. A light is not necessary if there is adequate ambient lighting.

The color determination unit 16 determines a color based on the color data received from the color sensor 50. In certain modes of operation, the color determination unit 16 can apply further processing algorithms, for example to address any deficiencies of the sensing process such as issues of color balance in the CCD.

At the second stage 62, the operator scans the abdomen of the pregnant woman with the transducer probe 4 to obtain image data for at least part of the fetus. This image data is received by the data receiving unit 15. At stage 64, the rendering unit renders a 3D fetal image, which is rendered using the determined color. At final stage 66, the rendered image is displayed on the main display screen 6 of the ultrasound machine 2.

The embodiment of FIG. 5 enables a color to be determined during the ultrasound scan, without the need for an extra step or interface. In some cases, the sensed color may also be more accurate. The color sensing may be automatic.

The process of determining a color for a fetal image based on a property of one parent of the fetus has been described. The property can be, for example, at least one of the skin color (sensed by a sensor or input by the operator), the ethnicity or the geographical location of the pregnant woman.

In further embodiments, the determined color is based on a first property of a first parent of the fetus and a second property of a second parent of the fetus. The first or the second property may be skin color, ethnicity, or geographical location, or any other suitable property. The first property and the second property do not need to be the same type of property. For example, a color may be determined that is based on the skin color of one parent and the ethnicity of the other.

Figure 7:
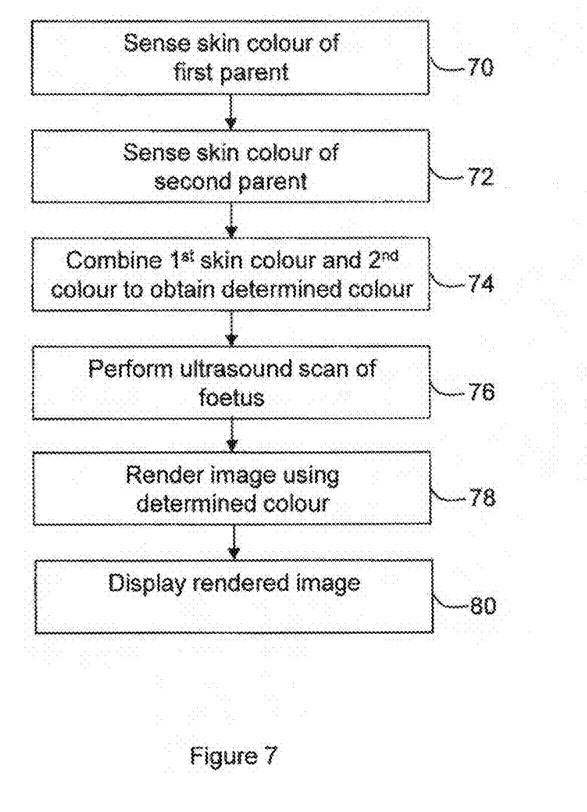
FIG. 7 is a flowchart illustrating in overview a mode of operation of an embodiment in which the skin color of two parents is measured.

The process of one embodiment is illustrated in the flow chart of FIG. 7. In this embodiment, both parents of the fetus are present at the ultrasound scan and the determined color is based on the skin colors of both parents.

A color sensor 50 (which may be located on a transducer probe 4 or on a separate unit) senses a first skin color of the first parent (stage 70) and a second skin color of the second parent (stage 72). Alternatively, two separate color sensors 50 may be used. For example, a color sensor on a transducer probe 4 may be used to sense the skin color of a pregnant woman, and a further color sensor to sense the skin color of the other parent. The color sensor or sensors pass color data to the color determination unit 16.

At stage 74, the color determination unit 16 determines a color by averaging the first skin color and the second skin color, or by any other appropriate method. Alternatively, the color determination unit 16 combines the first skin color and the second skin color in varying proportions to determine a plurality of determined colors. The plurality of determined colors may include, for example, the skin color of the first parent, the skin color of the second parent, and a range of intermediate values.

At stage 76, the operator scans the abdomen of the pregnant woman with a transducer probe 4 to obtain image data for at least part of the fetus.

At stage 78, the rendering unit 18 renders an image from the fetal image data using the color that has been determined from the two skin colors of the two parents. If a plurality of colors has been determined, then multiple images may be rendered in each of the plurality of colors.

At final step 80, the main display screen 6 displays the image that has been rendered using the determined color, or displays one or more of the multiple images that have been rendered from the plurality of determined colors.

For example, three images may be displayed on the main display screen 6 simultaneously, in which one image is rendered in the first parent's skin color, a second image is rendered in the second parent's skin color, and a third image in an intermediate color between the skin color of the two parents. In an alternative embodiment, a plurality of colors are determined based on the skin color of a single parent, and used to display a plurality of rendered images on the main display screen 6. A plurality of determined colors, used to render a plurality of images on the main display screen 6, may be based on any property or properties of the parent or parents In a further embodiment, after step 72 (measurement of the second skin color), the control screen 8 displays a color selection interface 42 in which the range of colors displayed comprises a range of colors that are obtained by combining the first skin color and the second skin color in varying proportions. The operator selects a color, which is used as the determined color for rendering the final image.

In another embodiment, the skin color of a parent is determined from a photograph of that parent by using a color sensor 50 such as a CCD to sense the skin color of the parent from a printed or displayed version of the photograph of the parent, and to pass color data to the color determination unit 16. In a further embodiment, the skin color of a parent is determined from a photograph of that parent by the color determination unit using an image processing program. The image processing program is configured to determine a skin color or colors from a digital version of a photograph, using any suitable image processing method, and to pass color data to the color determination unit 16, for example as an RGB, HSL or Pantone value.

In some modes of operation, the skin color of a parent is sensed on another occasion and stored in memory unit 20 rather than being sensed at the time of the fetal imaging. The fetal image data, first skin color and second skin color may all be obtained on different occasions and stored in memory unit 20, and the rendering performed on yet another occasion. A photograph can be used to provide data on the skin color of a parent who is not present at the scan.

In further embodiments, at least one of fetal image data, first skin color and second skin color is stored on a portable memory device such as a DVD or USB stick, and 3D rendering software is stored on the same or a different portable memory device. This may be used, for example, to allow parents to change the rendered color of a fetal scan image after the scan, for example on a home PC. In some such embodiments the software is configured to use an image capture device forming part of, or associated with, the user's computer to capture the skin colour of one or more the parents and to use the captured skin colour or colours when rendering the fetal scan image. Alternatively, the software can be used to process stored images of the parent or parents to establish the colour of the fetus in the rendered fetal scan image. The software comprises a rendering unit, a color determination unit and a data receiving unit. The units may, for example, be in the form of modules, sub-routines or functions of a software package, or piece or pieces of software.

Any embodiment that comprises a color selection interface, an ethnicity selection interface or a geographical selection interface may be varied for two parents. For example, a first color selection interface and a second color selection interface may be displayed, with the operator selecting a first skin color from the first interface and a second skin color from the second interface, based on the skin colors of the first and second parent respectively. Alternatively, a first and a second skin color may be selected from a single color selection interface 42, or the operator may select a single color based on the skin color of both parents (for example if both parents have similar skin colors, or by the operator's judgement of a color that is intermediate between the skin colors of the parents). Similar considerations apply to the ethnicity selection interface and the geographical selection interface.

Any property or properties of the first parent may be combined in any way with any property or properties of the second parent to result in one determined color or a plurality of determined colors. Skin color sensing may be combined with any of the selection interfaces described above.

It is known that the skin color of a newborn baby is typically lighter than the skin color that the baby will have as an adult, due to an increase in melanin in the skin over the first six months of life.

In a variant of any of the above embodiments, a first color is obtained that is based on at least one property of at least one parent. The first color may be obtained using a color sensor 50, by selection, by combination of the skin colors of two parents or by any other suitable method.

The color determination unit 16 then lightens this first color to determine a second color that is used in rendering the fetal image data. Alternatively, the operator selects on the color selection interface 42 a color that is lighter than the skin color of one or both parents, to represent the lighter skin color of a newborn baby.

In the embodiments described above, the determined color is determined before the fetal image is rendered and displayed. This is preferable because the image is only displayed in the determined color and not in any other color. The parent or parents may find it uncomfortable to see the fetal image change color, particularly where the image is a 4D real time image. However, in an alternative embodiment the fetal image is first rendered in a generic color (for example the standard sepia color) or an approximate color (for example, a color that is representative of a typical skin color related to the ethnicity of one or both parents) and then re-rendered in the determined color or colors. This may include changing the color of the image on the main display screen 6 in real time. Alternatively, the image on the main display screen 6 may be paused or removed from the main display screen 6 during the color selection process, or the main display screen 6 may be turned away from the parents. The image is then re-displayed in the determined color or colors.

All the embodiments above have described a process that relates to a human fetus. Embodiments also exist in which the fetus is an animal fetus. In this case, skin color may still be an appropriate property, or it may be replaced or supplemented by a color of hair, fur, wool or any other color property of an animal. Other properties include the breed of the parent animal or animals.

The skin, hair, fur, wool or other color of the or each parent animal is sensed by a color sensor as described above, or selected on a color selection interface, or a breed is selected on a breed selection interface. The color determination unit 16 determines a color or a plurality of colors based on the sensed or selected property. One or more determined colors is used to render one or more images of the animal fetus. In the case of a litter, a display of multiple images in a plurality of determined colors may represent the expected range of coloration of the animals in the litter.

The ultrasound machine may be a veterinary ultrasound machine that is configured to produce ultrasound images of animal fetuses, or any other suitable machine for obtaining fetal animal image data.

Embodiments have been described in which image data representative of a fetus is ultrasound image data. In alternative embodiments, other types of image data obtained using other modalities are used. Any suitable type of image data that can be rendered to provide a representation of the outer surface of the fetus can be used.

Whilst particular units have been described herein, in alternative embodiments two or more of those units can be embodied in a single unit, processing resource or other component, or a particular described unit can be provided in the form of two or more units, processing resources or other components in combination.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image data processing apparatus, comprising:
processing circuitry configured to:
receive image data that is representative of a fetus;
display a plurality of options relative to color to a user;
determine one standard color based on a selected option from the plurality of options by the user; and
render, using the determined standard color, an image of at least part of the fetus from the image data,
wherein the processing circuitry is configured to display each option representative of respective different human skin colors and determine the standard color based on the selection of one of the displayed plurality of options.

2. An apparatus according to claim 1, wherein the image data comprises ultrasound data, and the image data comprises one of 3D and 4D image data.

3. An apparatus according to claim 1, wherein the processing circuitry is configured to determine a first color based on a property of the parent of the fetus, to determine a second color by lightening the first color; and
to render using the second color the image of at least part of the fetus.

4. An apparatus according to claim 1, further comprising a memory configured to store the image data, and the processing circuitry is configured to receive the image data from the memory.

5. An apparatus according to claim 1, wherein the options include icons.

6. An apparatus according to claim 1, wherein the options include rendered image using color corresponding to the options.

7. An image processing apparatus, comprising:
processing circuitry configured to:
receive image data that is representative of a fetus,
display a plurality of options relative to property of ethnicity to a user;
determine a color based on at least one selected option from the plurality of options by the user; and
render, using the determined color, an image of at least part of the fetus from the image data.

8. An apparatus according to claim 7, wherein
the property of ethnicity is skin color; and
the processing circuitry is further configured to determine the color based on both a skin color of the first parent and a skin color of the second parent by combining the skin color of the first parent and the skin color of the second parent.

9. A method of producing a fetal image, comprising:
receiving image data that is representative of a fetus;
displaying to a user a plurality of options relative to color;
determining one standard color based on a selected option from the plurality of options by the user; and
rendering, using the determined standard color, an image of at least part of the fetus from the image data,
wherein the displaying displays each option representative of respective different human skin colors and the determining determines the standard color based on the selection of one of the displayed plurality of options.

10. A non-transitory portable computer memory device storing:
image data representative of a fetus; and
3D rendering software, wherein the 3D rendering software is configured to:
display to a user a plurality of options relative to color;
determine one standard color based on a selected option from the plurality of options by the user; and
render a fetal scan image from the image data using the determined standard color,
wherein the 3D rendering software is configured to display each option representative of respective different human skin colors and determine the standard color based on the selection of one of the displayed plurality of options.

* * * * *